United States Patent [19]

Flora et al.

[11] 4,207,520
[45] Jun. 10, 1980

[54] MULTIPLE FREQUENCY DIGITAL EDDY CURRENT INSPECTION SYSTEM

[75] Inventors: John H. Flora, Lynchburg, Va.; Henry T. Gruber, Columbus, Ohio

[73] Assignee: The United States of America as represented by the Secretary of the Air Force, Washington, D.C.

[21] Appl. No.: 893,869

[22] Filed: Apr. 6, 1978

[51] Int. Cl.² .......................................... G01R 33/00
[52] U.S. Cl. .................................... 324/238; 324/233
[58] Field of Search ............................. 324/219–220, 324/226–228, 232–234, 237–243, 260

[56] References Cited

U.S. PATENT DOCUMENTS

| | | | |
|---|---|---|---|
| 3,056,081 | 9/1962 | Hochschild | 324/238 |
| 3,422,346 | 1/1969 | Hammer | 324/241 |
| 3,675,118 | 7/1972 | Booth | 324/226 |
| 3,688,186 | 8/1972 | Judd | 324/237 |
| 3,701,941 | 10/1972 | Bantz et al. | 324/238 |
| 3,823,368 | 7/1974 | Mansson et al. | 324/233 |
| 3,826,976 | 7/1974 | Winston et al. | 324/233 |
| 4,006,407 | 2/1977 | Flaherty et al. | 324/233 |
| 4,083,002 | 4/1978 | Allport | 324/227 |

Primary Examiner—Rudolph V. Rolinec
Assistant Examiner—Walter E. Snow
Attorney, Agent, or Firm—Joseph E. Rusz; Henry S. Miller

[57] ABSTRACT

An apparatus for inspecting for cracks under installed fasteners and the like using a multiple frequency digital eddy current system. A computer with a plurality of digital arrays generate drive signals which are converted to analog and applied to the test coil, a second set of digital arrays generate balance signals, are adjusted in amplitude and phase and drive signals so that the output of the test coil is zero in a test specimen, output signals from a work piece are processed in the computer giving phase-sensitive crack detection.

8 Claims, 2 Drawing Figures

MULTIPLE FREQUENCY DIGITAL EDDY CURRENT INSPECTION SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to non destructive testing, and in particular, to a computerized system for eddy current testing using the phase and amplitude change in output signals for crack detection.

In the broad field of materials testing, be it non destructive or not, there is a constant effort to improve methods to achieve more accurate test results. Further, objects of improvements in this field aim toward providing methods and means for simplification of the testing process while maintaining a high degree of reliability in the test results.

One of the most important areas of non destructive testing resides in the aircraft industry. Aircraft, because of the high safety requirements, are tested regularly for metal fatigue and unusual or unexpected wear. In the case of fastener holes, it is common and practical to utilize inspection equipment operating on the eddy current principal. These detection devices have proven their value except in the situation where the inspection process does not call for a removal of the installed fastener. An example would be where a wing-splice occurs, and perhaps two layers of wing material are held in place by a titanium or steel fastener. Cracks developing under these fasteners cannot be detected with the convenience of an eddy current detection system without removal of the fastener. One of the reasons for this is that, to observe such discontinuities, the eddy-current detector must function at a relatively low frequency and all known detectors show much instability at these low frequencies. The convenience is lost in the lack of reliability of the instrument.

We have developed a new and improved eddy current detection system that is highly stable and reliable and will provide the convenience of the eddy current detector of the inspection for cracks under installed fasteners and other like devices.

SUMMARY OF THE INVENTION

The invention is directed to an appartus for inspecting for cracks under installed fasteners and the like using a multiple frequency digital eddy current system. According to the invention, a computer is disclosed having a plurality of digital arrays stored in its memory for generating drive signals for a test coil. The drive signals from the computer are passed through a digital to analog (D/A) converter, then through an amplifier before being applied to the test coil. Another set of digital signal arrays called balance arrays are also stored in the computer microprocesser memory. The amplitude and phase of balance array signals are adjusted with respect to the drive signals so that the sum of the output of the test coil and the balance signal is close to zero when the test coil is placed on an uncracked specimen. The balance signals are D/A converted and applied to a summing amplifier together with the output of the test coil. The output of the summing amplifier is passed through band pass filters which remove the harmonics of the drive signal produced by inherent nonlinearity of the test coil and the specimen. The filtered output of the summing amplifier is analog to digital (A/D) converted, whereupon it is fed back to the computer memory. The test coil is energized sequentially at various frequencies for several cycles to allow turn-on transients to decay, then energized again for several cycles during which measurements are made. The measurements are entered in the computer memory for processing. Software programs include two main programs and a number of subroutines for exciting the test coils and performing phase-sensitive crack detection of the response signals from the test coil.

It is therefore an object of the invention to provide a new and improved digital eddy current inspection system.

It is another object of the invention to provide a new and improved digital eddy current inspection system that provides a stable acquisition of eddy current response signals.

It is a further object of the invention to provide a new and improved digital eddy current inspection system with more reliable detection of cracks and more versatile automatic control of the inspection process than is currently known.

It is still another object of the invention to provide a new and improved digital eddy current inspection system having improved frequency and amplitude stability over known like systems.

It is still a further object of the invention to provide a new and improved digital eddy current inspection system that provides phase sensitivity stability.

It is another object of the invention to provide a new and improved digital eddy current inspection system where operating parameters are easily selected for current test conditions with a minimum change in hardware.

It is another object of the invention to provide an eddy current inspection system having highly stable eddy current operation at relatively low operating frequencies.

These and other advantages, features and objects of the invention will become more apparent from the following description taken in connection with the illustrative embodiment in the accompanying drawing.

DESCRIPTION OF THE PREFERRED EMBODIMENT

Figure 1:
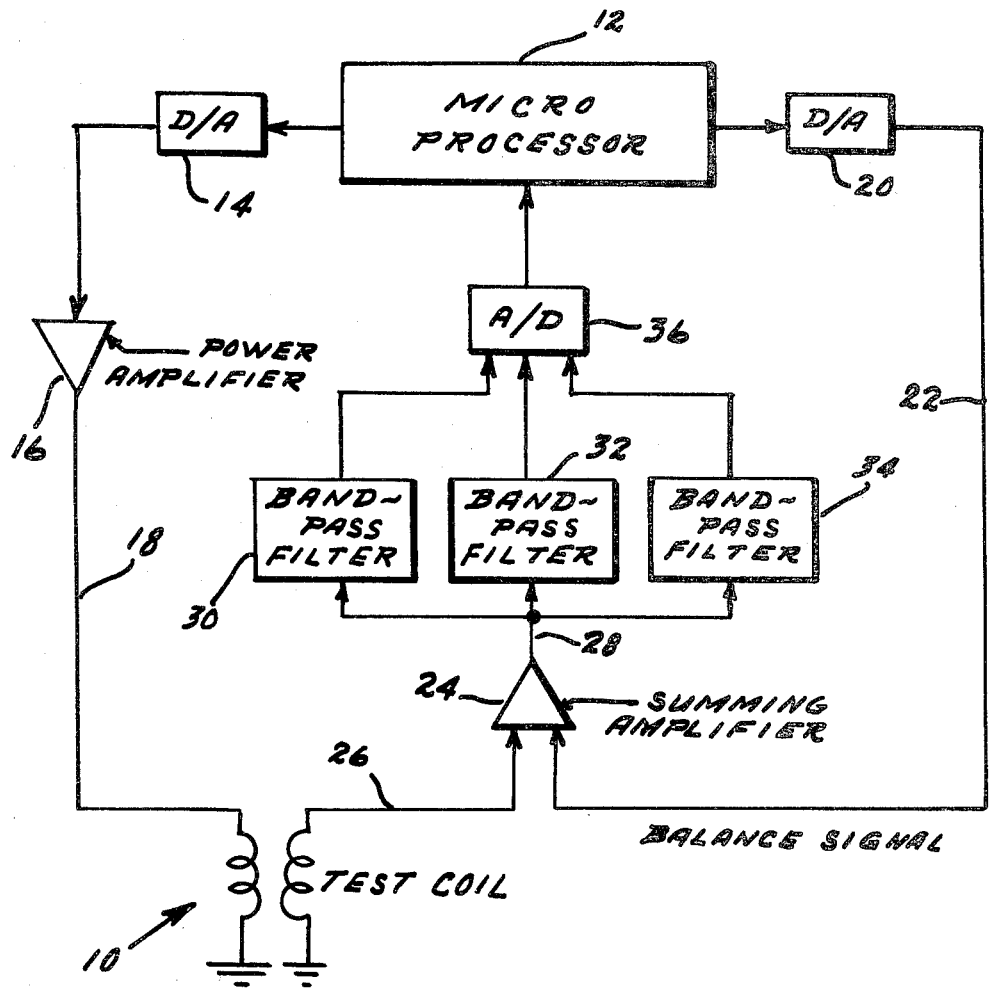
FIG. 1 is a block diagram of the system of the invention.

Referring now to FIG. 1, the eddy current test coil is shown generally at 10. Test coil drive signals are generated from digital arrays contained in the memory of the computer 12. The computing unit could be a conventional PDP 11/40 with a DEC/LB (Lab Peripheral System). This is done by outputting the digital value of the voltage level required to digital-to-analog converter (D/A) 14. The output of D/A (14) is amplified by power amplifier 16 and sent via line 18 to the test coil (10). A single cycle of the drive signal is stored in the digital drive array. Frequency is determined by the number of words in the drive array used to describe the cycle and the period of time between the loading of one number into the D/A buffer and the loading of the next number. The stepwise nature of the wave form generated is smoothed out by limiting the response of the power amplifier 16.

Computer 12 contains a second signal array, referred to as the balance array. A balance signal is generated in the same manner as the drive signal but power amplification is unnecessary. The balance signal is converted by the digital-to-analog (D/A) converter 20 and passed via line 22 to summing amplifier 24. The amplitude and phase of the balance signal are adjusted with respect to the drive signal so that the sum of the output of pick up coil (10) (via line 26) is close to zero. when the test coil is calibrated on the standard specimen, i.e. no crack condition.

The output 28 of summing amplifier 24 passes through band pass filters 30, 32, 34 and is coded in digital form by analog-to-digital (A/D) converter 36. The band pass filters (30, 32, 34) remove harmonics of the drive signal produced by the inherent nonlinearity of the test coil/specimen system. Measurements are stored in the memory of the microprocessor for later processing, or processing may be done in real time.

The problem of saturating the test coil by exciting it at all of the different frequencies at the same time is overcome by exciting the coil at the various frequencies sequentially. The coil is excited for several cycles to allow turn-on transients to decay. Measurements are then made during each of the frequencies so rapidly that for all practical purposes the measurements are simultaneous.

Stability in the phase of the measurement is high due to digital generation. For example, if a measurement is made at 90 degrees, and there are 400 words in the digital array, measurement is performed by the computer immediately after it has output the 100th word of the array. There is no significant phase variation since the measurement is always made at the same interval after the 100th word has been output. Quadrature measurements are exactly 90 degrees lagging the inphase measurement since the number of words in the drive arrays for the various frequencies is always a multiple of four, hence, in this case, a quadrature measurement would be made at the 200th word.

Figure 2:
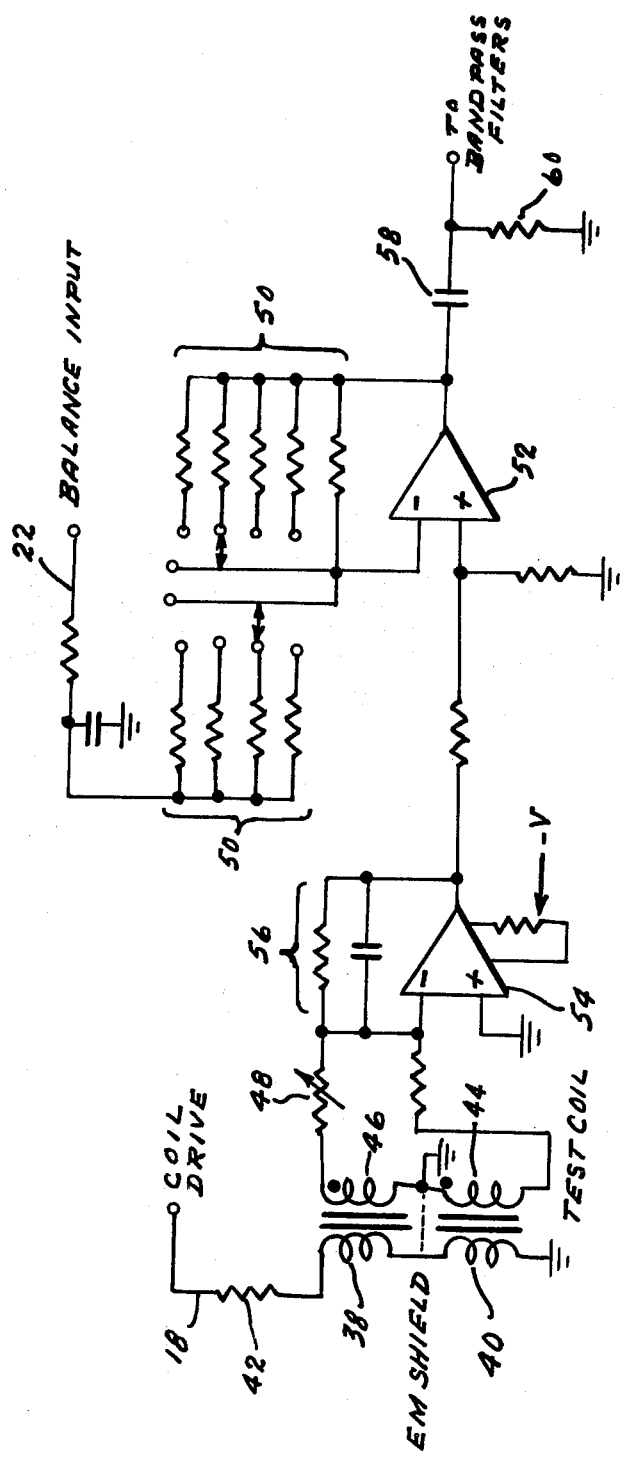
FIG. 2 is a schematic of the test coil interface network.

FIG. 2 discloses a proposed interface for the test coil (10) and the remainder of the test system as shown in FIG. 1.

The D/A output from microprocessor 12 is amplified by power amplifier 16 shown in FIG. 1. The output from the amplifier travels along line 18 to two series aiding drive coils 38, 40 through a series resistor 42, ideally 100 times or more greater in resistance than the impedance of the two coils (38, 40). Since the operational amplifier represents a constant voltage source, the series resistor provides a constant current source to drive the test coil.

Pick up and balance coils 44 and 46 respectively are connected to the remainder of the analog circuit. A variable input resistor 48 from balance coil 46 may be utilized to obtain a null in the output signal at the middle frequency with the test coil in place on a specimen, thereby eliminating the balance input signal from the computer.

System gain may be controlled by varying the feed back resistance 50 in operational amplifier 52. Changing the value of the feedback resistor changes the gains for both the error signal from input amplifier 54 and the balance signal by proportional amounts. The balance signal gain changes only the gain of the balance signal and permits the microprocessor to adjust the amplitude of the balance signal near the middle or upper half of the range of the digital-to-analog (D/A) converter 20, to provide good resolution of adjustment. RC filter 22 in the balance signal input removes the higher frequency components of the balance signal introduced by the stepwise changes from the digital-to-analog converter 20. The output of the system is AC coupled to the various band pass filters (30, 32, 34) through capacitor 58. Resistor 60 is connected to ground at the output and simply prevents any charge from building up on capacitor 58.

Although the invention has been described with reference to a particular embodiment, it will be understood to those skilled in the art that the invention is capable of a variety of alternative embodiments within the spirit and scope of the appended claims.

What is claimed is:

1. A multiple frequency digital eddy current inspection system for use in non destructive testing comprising: an eddy current test coil; a computer having a plurality of digital signal generating arrays for sequentially generating said multiple frequencies; means for changing digital signals to analog signals connected between the computer and the test coil; amplifier means for receiving eddy current signals from the test coil filter means connected to the amplifier means for selecting a desired signal; means having an input connected to the filter means for changing the filtered signal from an analog signal to a digital signal and an output connected to the computer for providing results of the eddy current inspection.

2. A digital eddy current inspection system for use in non destructive testing according to claim 1 wherein the computer generates multiple frequency drive signals and corresponding amplitude and phase adjusted balance signals.

3. A digital eddy current inspection system for use in non destructive testing according to claim 1 wherein the means for changing signals include digital-to-analog converters.

4. A digital eddy current inspection system for use in non destructive testing according to claim 1 including a power amplifier connected between the computer and test coil for driving the said test coil.

5. A digital eddy current inspection system for use in non destructive testing according to claim 2 wherein the amplifier means for receiving signals from the test coil includes a summing amplifier.

6. A digital eddy current inspection system for use in non destructive testing according to claim 5 wherein the summing amplifier receives the balance signals from the computer.

7. A digital eddy current inspection system for use in non destructive testing according to claim 1 wherein said filter means includes a plurality of band pass filters.

8. A digital eddy current inspection system for use in non destructive testing according to claim 1 wherein the means for changing an analog signal to a digital signal is an analog-to-digital converter.

* * * * *